(12) United States Patent
Herring

(10) Patent No.: US 12,263,036 B2
(45) Date of Patent: Apr. 1, 2025

(54) NON-INVASIVE DIFFUSE ACOUSTIC CONFOCAL THREE-DIMENSIONAL IMAGING

(71) Applicant: Rodney Herring, Victoria (CA)

(72) Inventor: Rodney Herring, Victoria (CA)

(*) Notice: Subject to any disclaimer, the term of this patent is extended or adjusted under 35 U.S.C. 154(b) by 1206 days.

(21) Appl. No.: 16/216,938

(22) Filed: Dec. 11, 2018

(65) Prior Publication Data

US 2019/0117189 A1 Apr. 25, 2019

Related U.S. Application Data

(63) Continuation-in-part of application No. 15/650,633, filed on Jul. 14, 2017, which is a continuation-in-part of application No. PCT/IB2016/050109, filed on Jan. 11, 2016.

(60) Provisional application No. 62/103,882, filed on Jan. 15, 2015.

(51) Int. Cl.
*A61B 8/14* (2006.01)
*A61B 8/00* (2006.01)
*A61B 8/08* (2006.01)

(52) U.S. Cl.
CPC .............. *A61B 8/145* (2013.01); *A61B 8/40* (2013.01); *A61B 8/4281* (2013.01); *A61B 8/4477* (2013.01); *A61B 8/4494* (2013.01); *A61B 8/5223* (2013.01); *A61B 8/0808* (2013.01); *A61B 8/085* (2013.01); *A61B 8/4218* (2013.01); *A61B 8/5269* (2013.01)

(58) Field of Classification Search
CPC ....... A61B 8/0808; A61B 8/085; A61B 8/145; A61B 8/40; A61B 8/4218; A61B 8/4281; A61B 8/4477; A61B 8/4494; A61B 8/5223; A61B 8/5269; G16H 50/30
See application file for complete search history.

(56) References Cited

U.S. PATENT DOCUMENTS

| | | |
|---|---|---|
| 5,760,901 A | 6/1998 | Hill |
| 6,132,375 A | 10/2000 | Napolitano |
| 6,193,663 B1 | 2/2001 | Napolitano et al. |

(Continued)

OTHER PUBLICATIONS

"Acoustic Imaging by Holography", MacAnally, R.B. et al., Aug. 1969 (Year: 1969).*

(Continued)

*Primary Examiner* — Christopher L Cook
(74) *Attorney, Agent, or Firm* — Baumgartner Patent Law, LLC; Marc Baumgartner

(57) ABSTRACT

A method and a device for imaging an object in a first material having a different optical density to the object. The method comprises: focusing an acoustic coherent beam to a virtual acoustic source in a fluid or an amorphous second material outside of the first material; moving the virtual acoustic source in the fluid or amorphous material such that at least a plurality of scattered beams from the virtual acoustic source scan the first material and at least one scattered beam is reflected from the object to form a reflected beam and at least one scattered beam bypasses the object to form a bypass beam, and wherein the reflected beam and the bypass beam intercept one another to form a coherent interference zone; and defocusing the coherent interference zone to provide a Fresnel fringe, the Fresnel fringe forming an image of the object.

6 Claims, 7 Drawing Sheets

(56) References Cited

U.S. PATENT DOCUMENTS

| | | |
|---|---|---|
| 6,436,046 B1 | 8/2002 | Napolitano et al. |
| 6,679,846 B2 | 1/2004 | Napolitano et al. |
| 7,639,365 B2 | 12/2009 | Herring |
| 8,485,034 B2 | 7/2013 | Herring |
| 2004/0059265 A1 | 3/2004 | Candy et al. |
| 2007/0171366 A1 | 7/2007 | Su et al. |
| 2007/0263226 A1 | 11/2007 | Kurtz et al. |
| 2008/0177183 A1 | 7/2008 | Courtney et al. |
| 2017/0311804 A1* | 11/2017 | Herring ............... G01S 7/52079 |

OTHER PUBLICATIONS

Canadian International Searching Authority, International Search Report mailed May 3, 2016, International Patent Application No. PCT/IB2016/050109, 6 Pages.

Canadian International Searching Authority, Written Opinion of the International Searching Authority mailed May 3, 2016, International Patent Application No. PCT/IB2016/050109, 6 Pages.

* cited by examiner

NON-INVASIVE DIFFUSE ACOUSTIC CONFOCAL THREE-DIMENSIONAL IMAGING

CROSS REFERENCE TO RELATED APPLICATIONS

This application is a Continuation-in-Part application of U.S. patent application Ser. No. 15/650,633, filed Jul. 14, 2017, which claims the benefit of International Application PCT/IB2016/050109, filed Jan. 11, 2016, which designated the U.S. and claims the benefit of priority to U.S. Provisional Application Ser. No. 62/103,882, filed Jan. 15, 2015, each of which is hereby incorporated in its entirety including all tables, figures, and claims.

FIELD

The present technology is a method of non-invasively scanning a body or body part to obtain a three-dimensional image, in which size, location and shape are determined. The method further allows a determination of the state of the body or body part. An apparatus for scanning is also provided.

BACKGROUND

The use of beams of radiation to obtain information about an object by detecting the amplitude or phase of the beam is well known for scientific and medical purposes. For example, the phase information of a beam that passes through an object can provide information on the object's temperature, composition, magnetic field or electrostatic field, whereas amplitude measurements can provide information on the opaqueness or density of the object. The beams are comprised of waves of radiation, where a wave, □, can be described as having both an amplitude, A, and phase, □ □ described mathematically as, $$\Phi = A \exp(\theta) \quad 1)$$

The information obtained from the method depends on whether it is detecting the amplitude or both the amplitude and phase of a beam's wave. If the method measures only a beam's amplitude, as is the case for X-ray, only density differences in the object are reported. This is a limitation of the technology as it does not provide information such as an object's temperature, composition, elasticity, strain field, magnetic or electrostatic fields. An additional disadvantage of a number of imaging techniques such as X-ray imaging methods is the strength of radiation employed. When used in diagnosis, the levels employed may have the potential to damage cells in the body.

Acoustic microscopes including Ultrasound are now widely used to image the inside of the body such as the fetus in the womb and blood flow in arties and veins. These microscopes emit a parallel acoustic beam that is reflected as a diffuse and scattered beam when it contacts surfaces such as bones and interfaces such as the interface between the embryonic fluid and the fetus. The reflected beams are used to measure the intensity of the acoustic beam. These microscopes cannot measure the intensity and phase of the beam passing through or reflected from soft tissue such as muscles or embryonic fluid. These microscopes also cannot measure temperature or composition as they only use the intensity of the acoustic beams and not the phase of the acoustic beams. Hence the images are not suitable for providing information other than that information that pertains to surfaces or interfaces. A further deficiency of these microscopes is that the image produced has a significant amount of background intensity caused by the diffuse scattering of beams after striking the surface or interface. Taking as an example, a prostate gland, an ultrasound image poorly identifies the interface between the prostate and other tissue and can also identify the urethra, however, it cannot identify any abnormalities within the prostate.

Another method that measures a beam's amplitude is confocal microscopy. Confocal scanning laser microscopes were developed in the 1980s for seeing three-dimensional objects. Confocal scanning laser microscopy uses a laser beam passing through an object to create a three-dimensional amplitude image of the object by detecting the amplitude of the beam through a pinhole aperture placed confocal with a point on a focal plane of the object.

Confocal microscopes have now found widespread applications in the materials, biological, and medical sciences. As a diagnostic tool, confocal microscopes are limited to detecting only thin tissue and the density differences of objects, which produce amplitude differences of the detected beam. The beams cannot penetrate far in to tissues and other materials. They do not measure the object's phase information. Hence, confocal microscopes cannot measure an object's composition or temperature.

If the method measures changes in the phase of a beam, then information can be provided about the object's temperature and composition. Acoustic beams can be used for this. The phase of acoustic beams are modified by an object's refractive index, where the refractive index is dependent on the object's temperature and composition and is a measure of the acoustic beam's speed of sound.

The absolute phase of an object can be measured using a Confocal Scanning Holography Microscope, as described in U.S. Pat. No. 7,639,365. This approach cannot be used to image the inside of the human body as laser beams do not readily pass through the human body.

The relative phase of an object can be measure using an Acoustic Confocal Interferometry Microscope, as described in U.S. Pat. No. 8,485,034. This approach requires an interference beam and a complex arrangement of mirrors and prisms and is not suitable for imaging the inside of the human body because of the geometric constraints.

Standard interferometry microscopes, standard holography microscopes, and standard holographic interferometry microscopes have been used to measure both the phase and the amplitude of objects, giving important information of objects such as their density, composition and temperature. These microscopes create a three-dimensional amplitude image and phase image of the object by measuring both the phase and the amplitude. As they are light microscopes the three-dimensional information measured from these microscopes comes only from the surface of the object and not at points within the object. In all cases, a reference beam and an object beam are used to collect data that results in the creation of the images. This limits the use of these microscopes to collecting data from or about surfaces of objects. In medical diagnosis they would therefore be potentially useful for diseases of the skin, but not for diseases of internal tissues or organs.

Other means able to measure the amplitude and phase of objects using an acoustic beam is spatially-filtered transmission ultrasound phase imaging as disclosed in U.S. Pat. Nos. 6,679,846, 6,436,046, 6,132,375 and 6,193,663. Spatially-filtered transmission ultrasound phase imaging involves measuring the amplitude and phase of an emitted beam and then again measuring the amplitude and phase of the acoustic beam after it passes through the object upon its arrival at a detector. The difference in amplitude and phase is attributed to the object. From the sound source, the beam diffusely scatters outward leading to background scatter that is not wanted. Within or around this background scatter will be the image of interest. That image is representative of the interfaces of the object being imaged. It does not represent a three dimensional image, nor can it locate diseased tissue within the tissue or organ of interest. Similarly, in materials, it cannot provide a three dimensional image nor can it show a different material within the material or a region having different physical characteristics within the material, unless there is an interface, such as the interface between a liquid and a solid.

United States Patent Application 20040059265 discloses noninvasively focusing acoustical energy on a mass such as a tumor within tissue to reduce or eliminate the mass. The presence of the mass in the tissue is detected by applying acoustic energy to the substance. The mass is localized to determine its position. Temporal signatures are developed to drive the acoustical energy on the mass. Dynamic focusing of the acoustical energy on the mass to reduce or eliminate it is accomplished utilizing the temporal signatures. Imaging of the mass is done using standing ultrasound imaging techniques (use of multiple parallel beams from an acoustic source outside of the body of the patient that are reflected off the object of interest in the body to provide intensity information [this reflected signal is referred to as a virtual source, but is not a source]) then either modeling or time reversal is used for driving acoustical energy which is then focused on the mass to treat the mass. The deficiencies in this method include the fact that it is based on models and assumptions, the imaging of the mass is not better than the images obtained with ultrasound, as that is how they image, and the information attainable using the method are limited. Also, as the three-dimensional position cannot be determined, when used to treat a mass, such a treatment is reliant on the models and assumptions or time reversal to be being correct.

It would be advantageous to provide a device, system and method that can detect both the amplitude and phase of a beam. Such a device, system and method would be able to provide information on the object's density, temperature, composition, elasticity, strain field, magnetic or electrostatic fields. This is of great significance in the medical field, as of being able to obtain information on density, temperature, and composition allows one to be able to potentially diagnose, treat and assess effectiveness of treatments for diseases such as cancer. Ideally, the device would be suitable for being hand-held, with a variety of different shaped detector holders for application to different parts of the body, for example, but not limited to the prostate, breast, head, and skin. It would be advantageous if the same beam used to detect and provide a three-dimensional image of the object could be used to treat the object.

Examples of an application where the measurement of temperature and composition is important include medical diagnostics aimed at understanding the function of organs, tissue and diseased regions in the body. Presently medical researchers do not have good means to non-invasively measure the internal temperature and composition of the body. It is an object of the present technology to provide such capabilities.

SUMMARY

The present technology provides a method of creating three-dimensional images of objects of one optical density in another object of a different optical density that is far superior to ultrasound methods. A coherent beam is focused into a virtual source outside of the objects and within a fluid or an amorphous material. By creating an interference zone of a bypass beam and a reflected beam, an interference zone can be created. This interference zone is defocused to provide the three-dimensional image.

In one embodiment, a method of imaging an object in a first material having a different optical density to the object is provided, the method comprising: focusing an acoustic coherent beam to a virtual acoustic source in a fluid or an amorphous second material outside of the first material; moving the virtual acoustic source in the fluid or amorphous material such that at least a plurality of scattered beams from the virtual acoustic source scan the first material and at least one scattered beam is reflected from the object to form a reflected beam and at least one scattered beam bypasses the object to form a bypass beam, and wherein the reflected beam and the bypass beam intercept one another to form a coherent interference zone; and defocusing the coherent interference zone to provide a Fresnel fringe, the Fresnel fringe forming an image of the object.

The method may further comprise an acoustic detector detecting the image of the object.

The method may further comprise moving the virtual acoustic source in the fluid or amorphous material such that at least one scattered beam passes through the object to become an object beam and is detected by the acoustic detector.

The method may further comprise comparing the phase of the object beam with the phase the bypass beam to provide information about the object.

The method may further comprise comparing the amplitude of the object beam with the amplitude of the bypass beam to provide information about the object.

In the method the information from the phase may be the temperature, composition, magnetic field or electrostatic field of the object and the information from the amplitude may be the optical density of the object.

In the method, the speed of sound of the object may be determined.

In the method, the speed of sound of the object may be used to identify the object.

In the method, the object may be identified as a tumour or lesion in the first material.

In the method, the acoustic coherent beam may be focused in a fluid or amorphous second material in the body of a patient.

In the method, the acoustic coherent beam may be focused in one of urine in the bladder, fatty tissue, brain tissue, peritoneum fluid, stomach fluid, the gall bladder and the spleen.

In the method the acoustic coherent beam may be focused in a fluid outside of the body of a patient in which at least the part of the body of interest is immersed.

In another embodiment, a system for imaging an object in a first material of different optical density to the object is provided, the system comprising: a coherent acoustic beam source which emits a coherent acoustic beam; a focuser positioned to focus the coherent acoustic beam to a virtual acoustic imaging source, the virtual acoustic imaging source emitting scattered beams; a coherent acoustic beam source actuator in mechanical communication with the coherent acoustic beam source; a focuser actuator in mechanical communication with the focuser; a processor in electronic communication with the coherent acoustic beam source actuator and the focuser actuator; a memory in communication with the processor and having instructions thereon to instruct the processor to move the coherent acoustic beam source and the focuser such that at least some of the scattered beams are reflected off the object to be reflected beams and pass by the object to be bypass beams and such that the reflected beams and the bypass beams form an interference zone, the memory further configured to produce the coherent acoustic beam and the focuser to produce a Fresnel fringe in the interference zone; and an acoustic detector positioned to image the Fresnel fringe.

In the system, the memory may include instructions for the processor to sharpen the image.

The system may further comprise a spatial filter in front of the acoustic detector.

The system may further comprise a cone reflector, the cone reflector between the coherent acoustic beam source and the focuser.

The system may further comprise a pair of articulating arms, each with a distal end, and a second acoustic detector, each acoustic detector mounted on an arm, proximate the distal end.

The system may be sized for imaging ovaries.

FIGURES

DESCRIPTION

Except as otherwise expressly provided, the following rules of interpretation apply to this specification (written description and claims): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, the terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Figure 1:
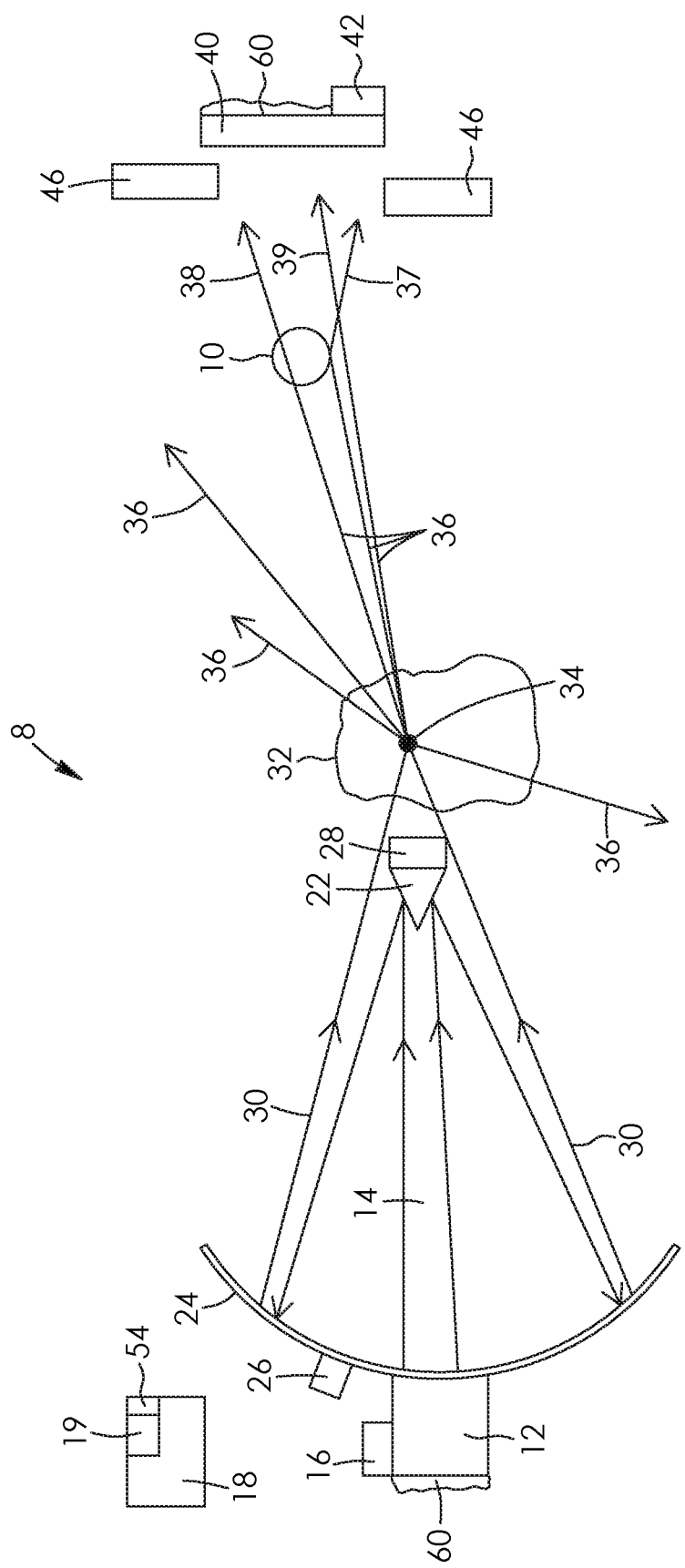
FIG. 1 is a schematic of the operation of a diffuse acoustic confocal three-dimensional imaging device of the present technology.

An overview of the system, generally referred to as 8, for imaging a tissue, an organ, or a body part (an object), generally referred to as 10, is shown schematically in FIG. 1. It creates and uses the scattered beams that are considered to be noise (speckle noise). A coherent acoustic source 12 such as a coherent acoustic emitter emits a single coherent acoustic beam 14. The coherent acoustic source 12 can be manually moved or can be moved with a source actuator 16 that is in mechanical communication with the coherent acoustic source 12. The source actuator 16 is preferably controlled by a processor 18, which is under control of a memory 19, which has instructions thereon for instructing the processor 18 to actuate the source actuator 16. The coherent acoustic source 12 provides a coherent acoustic beam 14 with a beam frequency between and including about 0.5 megahertz and about 100 megahertz for obtaining information including one or more of density, temperature, composition, elasticity, or strain field in a mammalian body.

The coherent acoustic beam 14 has a large cross-sectional area, typically on the order of a centimeter or a few centimeters. The coherent acoustic beam 14 is directed to a cone shaped reflector 22 and then to a focusing mirror or lens 24 where it is reflected by a curved surface and focused into a convergent beam 30 that is transmitted into a fluid or amorphous medium 32. The focusing mirror 24 pivots under control of a focusing mirror actuator 26, which is under control of the processor 18, which in turn is controlled by the memory 19, which has instructions thereon for instructing the processor 18 to actuate the actuator 26. The cone shaped reflector 22 is under control of an actuator 28 that moves it towards and away from the acoustic emitter (source) 12. The actuator 28 which is under control of the processor 18, which in turn is controlled by the memory 19, which has instructions thereon for instructing the processor 18 to actuate the actuator 28. In one embodiment, the fluid or amorphous medium 32 is within the body and is, for example, but not limited to, urine in the bladder, fatty tissue, brain tissue, peritoneum fluid, stomach fluid, the gall bladder and the spleen. The convergent beam 30 converges to a point which is a virtual focused acoustic imaging source 34 at the point of cross-over. The processor 18 under control of the memory 19 is configured to direct the source actuator 16 to cause the coherent acoustic source 12 to move the source 34 into the fluid or amorphous medium 32 and to move it around within the fluid or amorphous medium 32. Further, the processor 18 under control of the memory 19 is configured to move the cone shaped reflector 22 towards and away from the focusing mirror 24, thus moving the virtual source 34 towards and away from the acoustic emitter 12, again positioning the virtual source 34 in the fluid or amorphous medium 32. The virtual source 34 is located outside of the object being imaged and inside the fluid or amorphous medium 32. The source 34 transmits a plurality of beams 36 that are scattered in all directions three-dimensionally. The scattered beams 36 pass out of the medium 32. By moving the source 34 in the fluid or amorphous medium 32, the plurality of beams 36 scan around outside of the medium 32. The beams 36 enter into any object 10 that they encounter, then out of the object 10 as object beams 38, which are detected by an acoustic detector 40. The acoustic detector 40 is aimed at the source 34 such that it can detect the object beams 38. The object beams 38 are refracted as they pass through the object 10. The acoustic detector 40 can move to collect object beams 38 having a range of angular directions. The object beams 28 are refracted as they pass through the object 10. The acoustic detector 40 moves towards and away from the object 10 in order to defocus the image created by combinations of reflected beams 37 and bypass beams 39, such that it becomes photographically visible. A detector actuator 42 is in mechanical communication with the acoustic detector 40 and is under control of the processor 18 that is in electronic communication with the detector actuator 42. Again, the processor 18 receives instructions from the memory 19. The object beams 38 also contain information about the object 10. The information carried by the object beams 38 is analyzed to determine its amplitude and phase according to techniques known in the art. The phase information of the object beam 38 provides information on the object's temperature, composition, magnetic field or electrostatic field and amplitude measurements provide information on the opaqueness or density of the object. A spatial filter 46 reduces the noise from unwanted scattered beams 36 and is located in front of the acoustic detector 40.

A couplant 60 is used between the patient and each of the coherent acoustic source 12 and the acoustic detector 40. Alternatively, the patient may be immersed in fluid, or the relevant part of the patient may be immersed in fluid, such that there is a fluid interface between the patient and the device 8. In order for the object 10 to be observed, the source 34 is moved inside the medium 32 by pivoting the focusing mirror 24 and the acoustic detector 40, or by shifting the microscope 6, or by repositioning the patient. A vector network analyzer is not required as the amplitude and phase information of the emitted and received intensities is not used to produce the image. However, a better intensity image can result using the vector network analyzer for the temporal filter. An intensity image using Fresnel fringes will form without using the temporal filter and spatial filter but using these filters the intensity image will improve, i.e., better spatial resolution, by being able to reduce the apparent size of the virtual source.

For phase or speed of sound imaging, the vector network analyzer is needed to measure the time difference for receiving the acoustic beam at each element in the detector. Since the path length traveled by the acoustic beam from the emitter/lens assembly to the detector, by measuring the time using the vector network analyzer, the speed (m/s) can be determined.

Figure 2B:
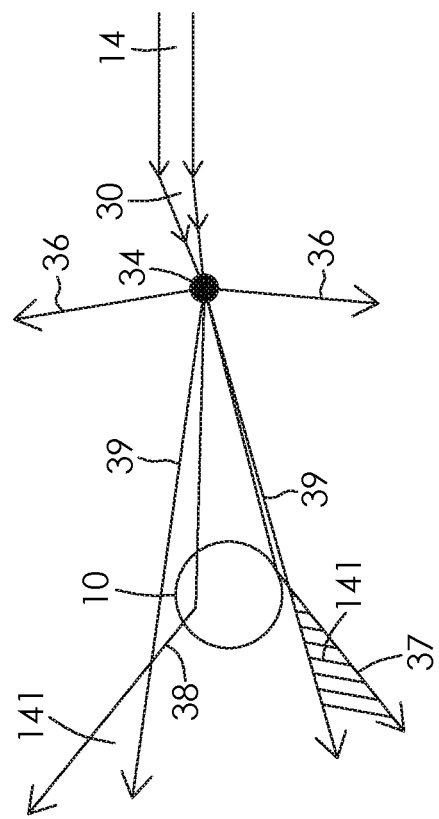
FIG. 2B is a schematic showing the beams used in the present technology.
Figure 2A:
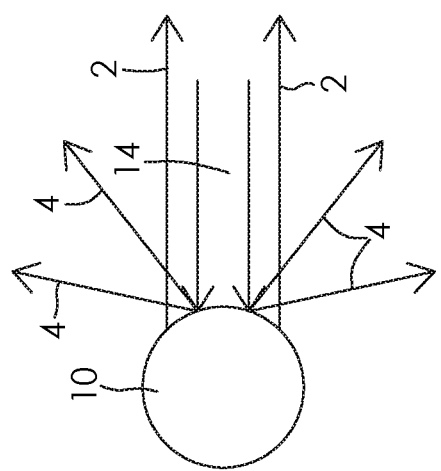
FIG. 2A is a schematic showing the beams used in a prior art ultrasound imager.

FIGS. 2A and 2B show a comparison of the beams and how they produce an image in a prior art ultrasound (2A) and in the present diffuse acoustic confocal imager (2B). The coherent beam 14 strikes the object 10 and produces reflected beams 2 and scattered beams 4. The reflected beams 2 produce the image (noting that a relatively large difference in refractive index between the tissue types is needed to identify the interface, and that only the interface is identified). The scattered beams 4 produce noise that needs to be removed in order to produce a clean image.

Using the diffuse acoustic confocal imager, the emitted coherent beam 14 is very flat (spatial coherence) and are constant (temporal coherence). The coherent beam 14 is focused to a convergent beam 30 which converges to a point, the virtual source 34, which emits scattered beams 36. The virtual source 34 can be moved around to allow the scattered beams 36 to hit the object 10 from many spots, distances and angles. The scattered beams 36 do one of miss the object 10, hit the edge of the object and reflect off the edge or pass through the object 10.

Those that are reflected off the object are referred to as reflected beams 37. Those that pass through the object are referred to as the object beams 38. Those that miss the object but overlap with the reflected beams 37 are called bypass beams 39.

The object beams 38 can be considered for diagnostic purposes of the object 10. To form a speed of sound image using temporal coherence, the emission time of the beam is measured and then the arrival time of the beam at each pixel in the image is measured. Any differences in the speed of sound across the image can be used to diagnose structures in the image.

The spatial coherent interference between the reflected beams 37 and the bypass beams 39 in the overlap is used to create the image. The image of the object 10 can be considered as an inline hologram for diagnostic purposes of the object 10. More specifically, the image is created using the principle of Fresnel diffraction. The bypass beam 39 overlaps with the reflected beam 37 to produce an interference zone 141. This interference zone 141 between these two beams form the Fresnel fringe or defocus fringe. The retention of coherence in the bypass beam 39 and the reflected beam 37 is required for forming an interference fringe or Fresnel fringe in the image. Some intensity in the defocus or Fresnel fringe also comes from the refracted object beams 38 exiting the object 10 and interfering with the bypass beam 39 in the same manner in which the bypass beam and the reflected beam interfere although the refracted object beam has a less significant role in the image formation process of the Fresnel fringe.

The Fresnel diffraction produces a fringe (Fresnel fringe) in an acoustic image when defocusing occurs. The Fresnel fringe enhances the contrast between the forms and the background and allows for the imaging of soft tissues, and the interface between different soft tissues. This includes tissues that have very little difference in refractive indexes, such as for example, but not limited to, breast tissue and milk glands in the breast tissue, lesions in tissues, an egg in a fallopian tube.

The width of the overlap increases with defocus, which increases the width of the Fresnel fringe. The defocus decreases to zero where the object and camera are on the same plane. In this condition, the object disappears and can't be seen because a fringe cannot be made as there is no overlap.

Additionally, the spatial resolution is determined by the width of the Fresnel fringe. The smallest width of the Fresnel fringe found in the image is the size of the virtual source size. The size of the virtual source is determined by the focusing ability of the emitter/lens assembly and the wavelength of the emitted beam from the emitter. The resolution can approach the wavelength of the acoustic beam, which for a 50 MHz acoustic beam approaches the size of the cell (lamda=frequency/speed=50,000,000 per second/1500 m/s=0.00003=30 microns). This is much higher resolution than ultrasound.

An image formed with a large defocus, i.e., broad fringe lines, can be processed with the processor to sharpen the features (i.e., the Fresnel fringes) in the image by applying a defocus amount, delta f, and knowing the cone angle, alpha of the beam such that the reduction in fringe width is delta f times ½ the cone angle. Likewise, knowing the cone angle and the change in fringe width by a known or measured defocus can be used to determine the distance or position of the object, z, in the image, enabling a 3D image to be produced since the lateral dimensions, x, y, are already measurable in the image. This is one more advantage of a transmission image as produced by the present technology versus a reflected image (ultrasound). Ultrasound acquires z by a complex reflected time measurement of the reflected beam.

The distance between the virtual source 34 and the object 10 determines the magnification of the object. The further the virtual source 34 is to the object 10 the closer the magnification approaches one. The magnification of the object increases the closer the virtual source 34 approaches the object 10.

The spatial filter 46 and a temporal filter 54 (see FIG. 1), which is provided by the software in the memory 19, restrict the volume of the acoustic virtual source 34 used for imaging, with the smaller the volume, the better the resolution for imaging. The spatial resolution, in part, is set by the size of the convergent beam 30 at the focused virtual source 34. The spatial filter 46 defines a lateral x,y dimension or angular acceptance angle of the virtual source 34. The spatial filter 46 can be made smaller than the virtual source 34 and is one of the factors that determines the spatial resolution. It can be the determining factor that determines the spatial resolution in the x,y plane. The temporal filter 54 determines the z or axial spatial resolution of the virtual source 34. It determines the acceptance time for receiving the acoustic signal, start time and stop time.

Figure 3:
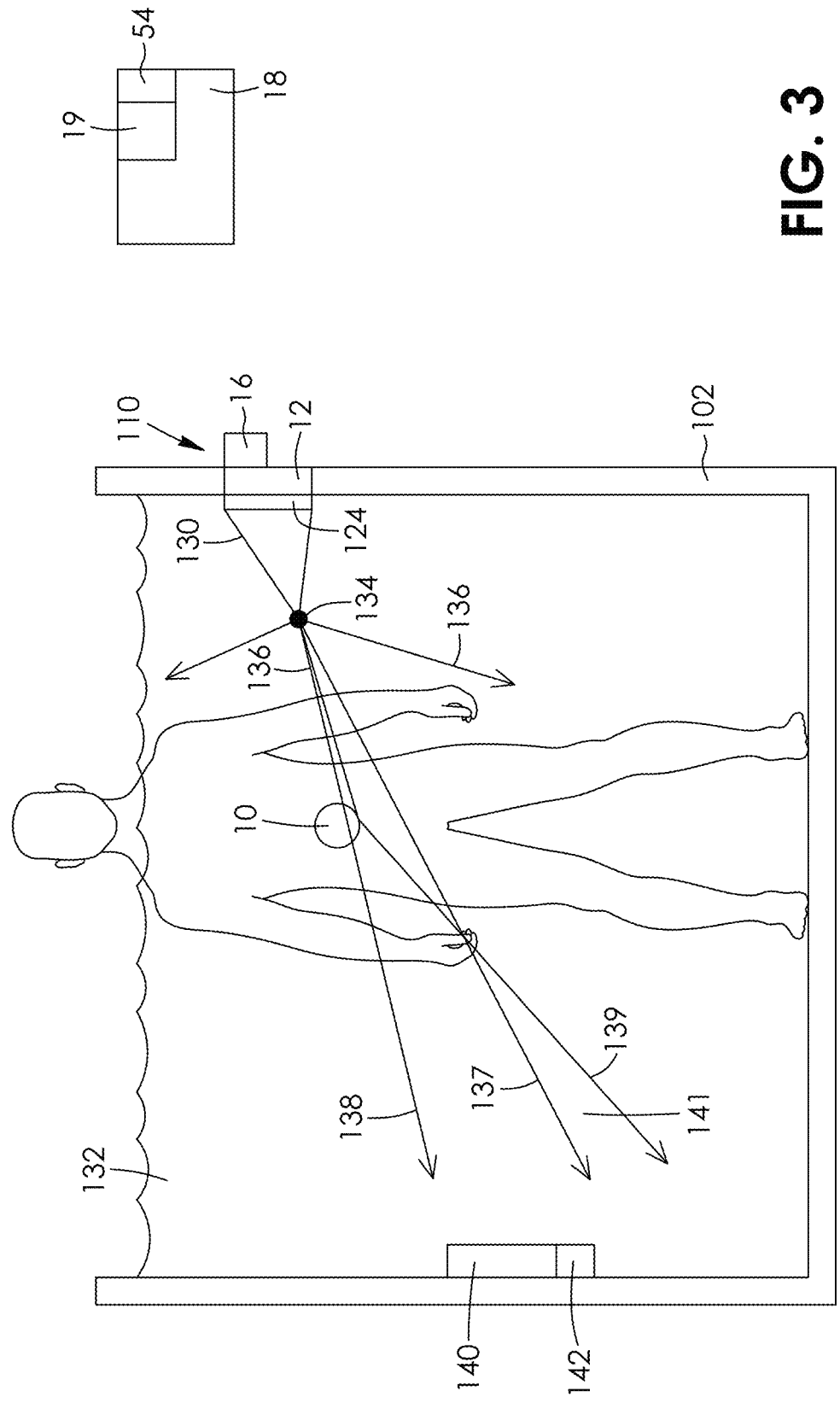
FIG. 3 is an embodiment of a detection system of the present technology.

In an embodiment shown in FIG. 3, the fluid or amorphous medium 132 is outside the person and is contained in a container 102. The container 102 is preferably adjustably attached to the device 110. The components of the system are as described above. The convergent beam 130 converges to a point which is a virtual focused acoustic imaging source 134 at the point of cross-over. The processor 18 is under control of the memory 19 which is configured to direct the processor to move the source actuator 16 to cause the coherent acoustic source 12 to move the virtual source 134 into the fluid or amorphous medium 132 and to move it around within the fluid or amorphous medium 132. The virtual source 134 transmits a plurality of beams 136 that are scattered in all directions three-dimensionally. These scattered beams 136 pass out of the medium 132. By moving the virtual source 134 in the fluid or amorphous medium 132, the plurality of scattered beams 136 scan around outside of the medium 132. Depending on the angle of incidence, the scattered beams 136 enter into any object 10 that they encounter, and pass through the object 10 and are detected as object beams 138 by an acoustic detector 140. Other scattered beams 136 are reflected off the object 10 and are called reflected beams 137. The scattered beams 136 that miss the object but overlap with the reflected beams 137 are called bypass beams 139. The acoustic detector 140 is focused on the source 134 and is located such that it can detect the plurality of scattered beams 136 that are proximate the object 10. The source 134 is moved within the medium 132 as needed to get a complete image of the object 10. The acoustic detector 140 can move to collect scattered beams 136 having a range of angular directions as indicated in FIG. 1. A detector actuator 142 is in mechanical communication with the acoustic detector 140 and is under control of a processor 144 that is in electronic communication with the detector actuator 142. The coherent interference between the reflected beams 137 and the bypass beams 139 in the overlap (interference zone 141) is used to create the image. The image of the object 10 can be considered as an inline hologram for diagnostic purposes of the object 10. The information carried by the object beams 136 can also be analyzed by the processor 18 to determine its amplitude and phase according to techniques known in the art. The amplitude and phase are compared with the amplitude and phase of a bypass beam 139.

In order for the object 10 to be observed, the source 134 is moved inside the medium 132 by pivoting the focusing mirror 124 and the acoustic detector 140, by moving the device 110, or by repositioning the patient. If the object 10 is, for example, a disease, a mass, a tumour, a growth or the like, the coherent interference between the reflected beams 137 and the bypass beams 139 in the overlap (interference zone 141) is used to create the image of the object. The Fresnel fringe is what creates the image and is caused by defocusing, as described above.

Figure 4:
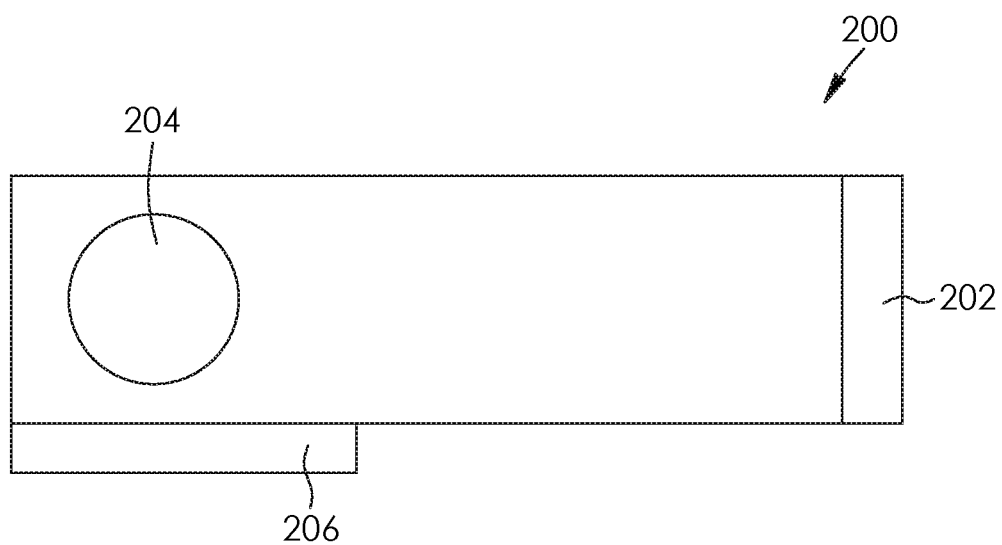
FIG. 4 is an embodiment for imaging an ovary using the present technology.
Figure 5:
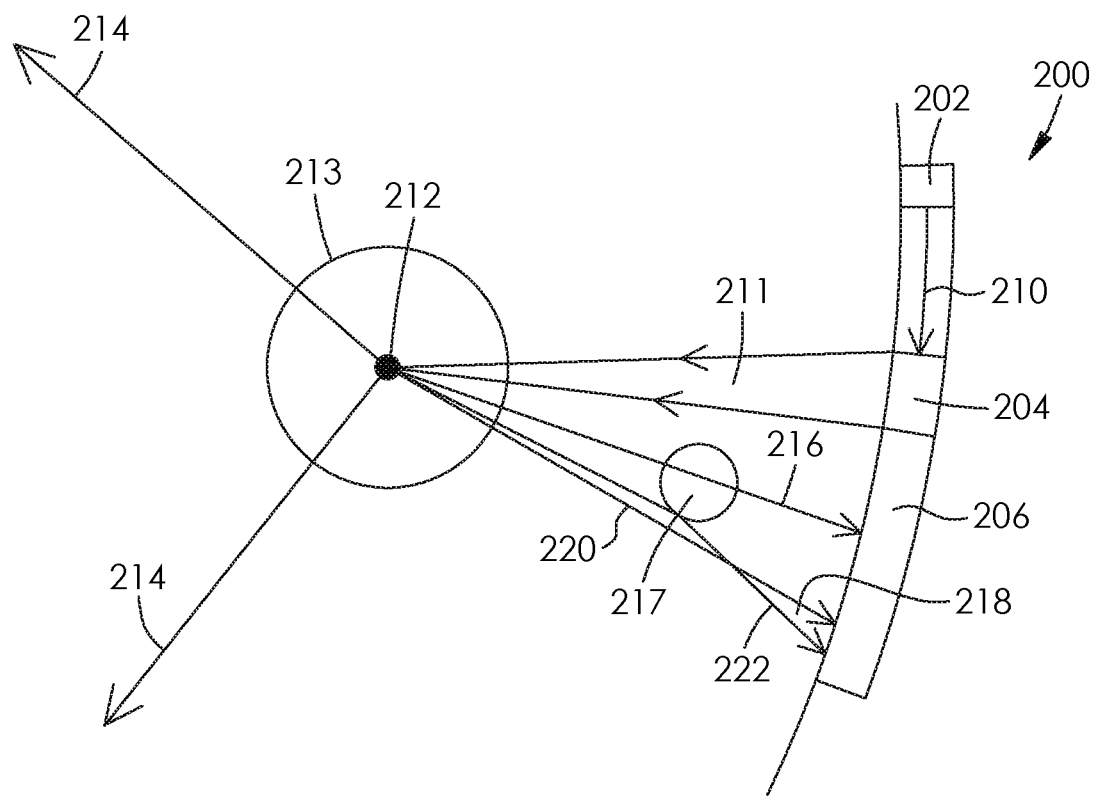
FIG. 5 is a schematic of the operation of the diffuse acoustic confocal three-dimensional imaging device for scanning an ovary using the embodiment of FIG. 4.

As shown in FIG. 4, in one embodiment, a device 200 for imaging the ovary is provided. The acoustic emitter 202 is located at one end of the device and a focusing mirror 204 is located at or proximate the other end of the device 200. An acoustic detector 206 is aligned with the ovary. The detector 206 may be a linear array detector. A schematic is shown in FIG. 5. As described above, a coherent beam 210 is emitted by the acoustic emitter 202 and is focused by the focusing mirror 204 into a convergent beam 211 that results in a virtual source 212, which in turn produces scattered beams 214 in three dimensions. The acoustic detector 206 detects object beams 216, which are the beams that pass through the object 217, which in this case is the ovary. The acoustic detector 206 also detects the Fresnel fringe 218 which is produced by bypass beams 220 and reflected beams 222, as described above. The virtual source 212 is positioned in the bladder 213 and is moved around so that the scattered beams 214 scan around until the ovary is found. The scattered beams 214 then reflect and become reflected beams 222, bypass the ovary to be bypass beams 220 and pass through the ovary to become object beams 216.

Figure 6:
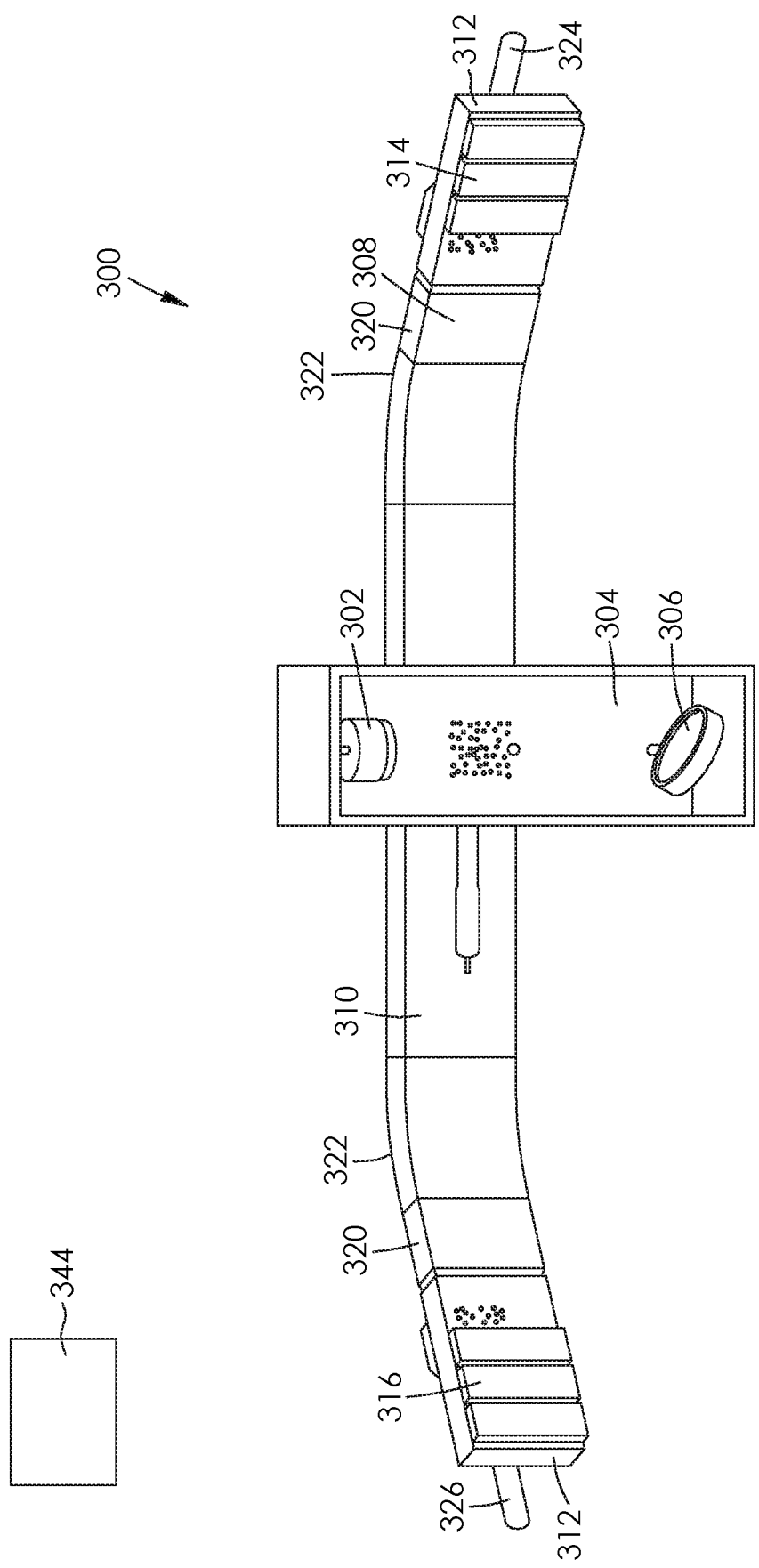
FIG. 6 is an embodiment for imaging both ovaries using the present technology.

As shown in FIG. 6, a device 300 for imaging both ovaries is provided. The acoustic emitter 302 is centrally located in a vertical housing 304 which also houses the focusing mirror 306. The device 300 has two arms, a right arm 308 and a left arm 310. Proximate the ends 312 of the arms 308, 310 are located a right detector 314 and a left detector 316, respectively. The arms 308, 310 include articulating segments 320 that are under control of mechanical manipulators 322. As a further means of detecting the beams, a right detector actuator 324 and a left detector actuator 326 are in mechanical communication with the acoustic detectors 314, 316 and is under control of a processor 344 that is in electronic communication with the detector actuators 324, 326.

Figure 7:
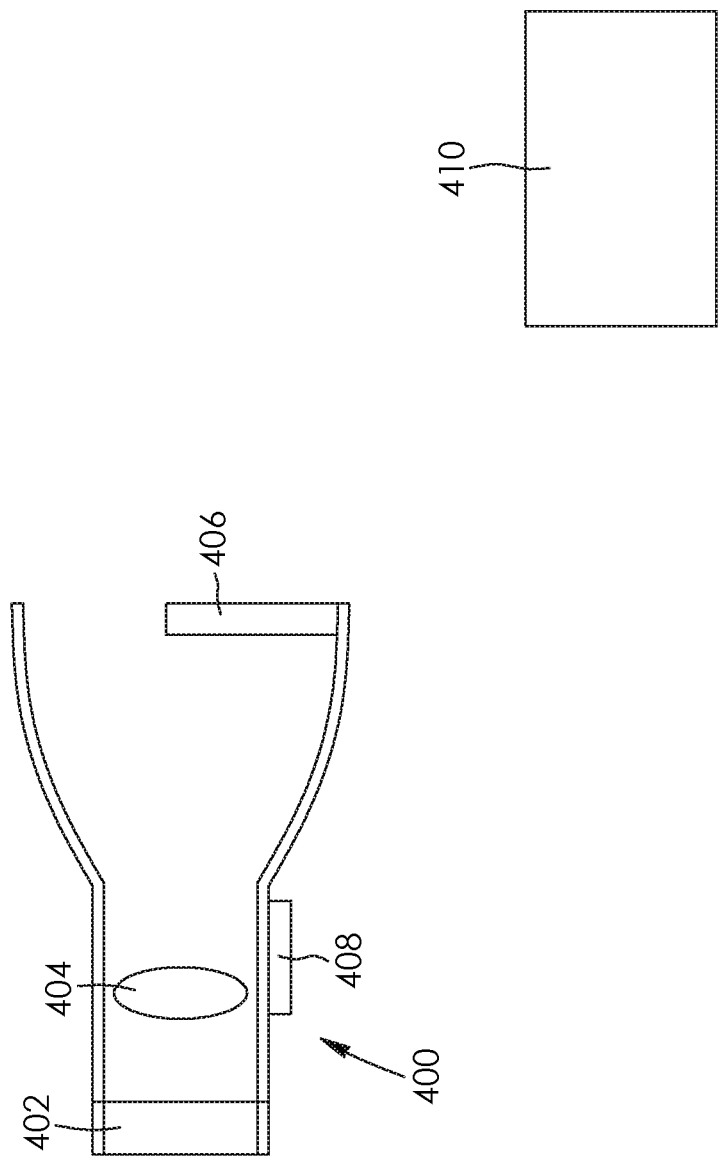
FIG. 7 is an embodiment for imaging a breast using the present technology.

As shown in FIG. 7, a handheld device 400 for imaging the breast is provided. It includes an acoustic emitter 402, a focusing mirror 404 and an acoustic detector 406 arranged as described above. It is manually controlled and has a Bluetooth radio 408 for communicating with a processor 410.

Figure 8:
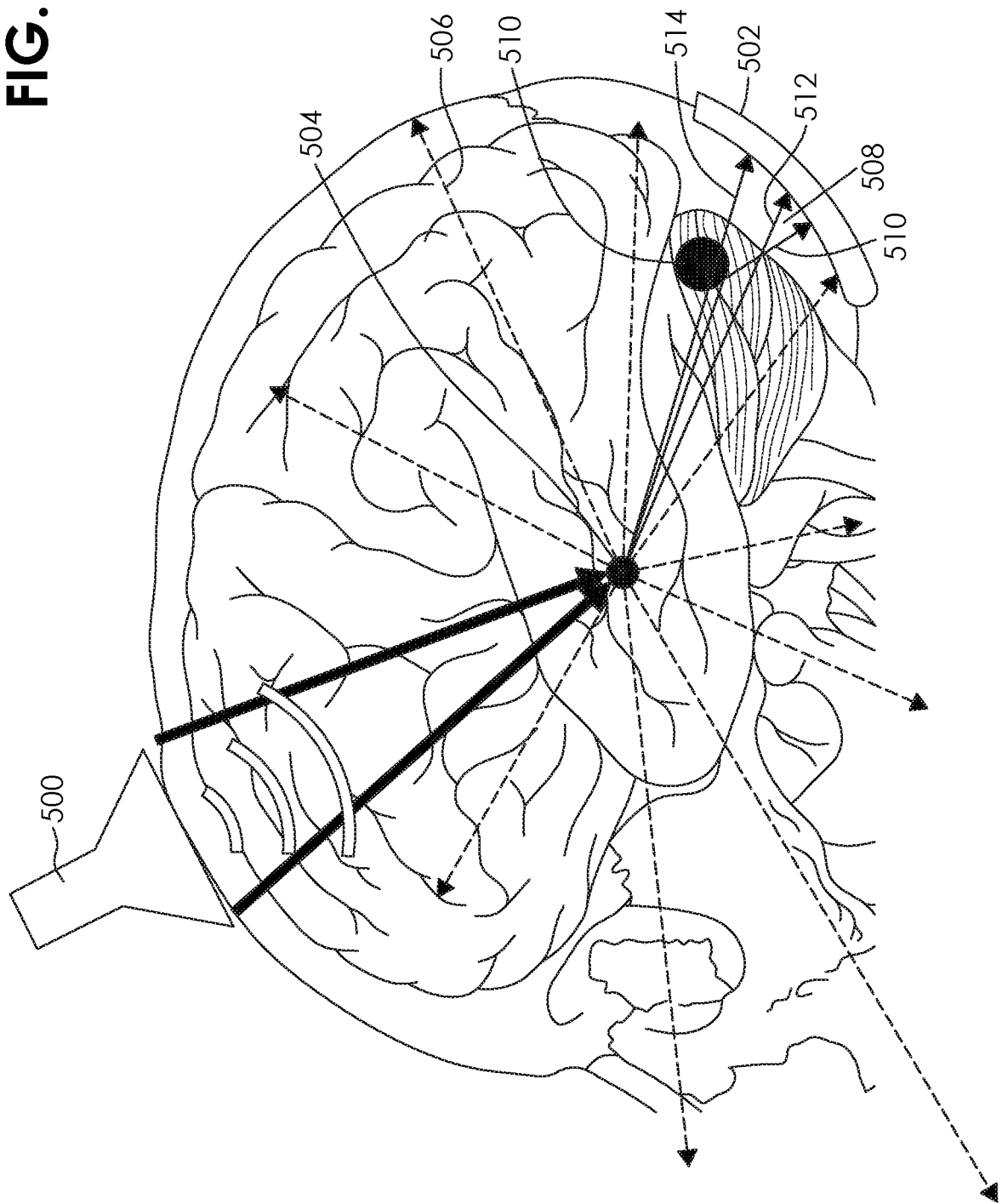
FIG. 8 is an embodiment for imaging the brain using the present technology.

As shown in FIG. 8, a system including a handheld emitter device 500 can be used to image the brain. The detector or detectors 502 are placed as needed and can be retained in position simply by the patient leaning their head on the detectors. The virtual source 504 is focused on the fatty tissue of the brain and the scattered beams 506 are emitted in three dimensions from the virtual source 504. The beams that go through the object 510 are object beams 514. Again, the image is created by defocusing the interference zone 508 between the reflected beams 510 and the bypass beams 512.

In all embodiments, the method involves the acoustic emitter emitting 600 a coherent beam which is optionally reflected by the cone shaped reflector, which can be moved in and out by an actuator. The beam is focused by the focusing lens or mirror into a virtual source in an amorphous material or fluid. The virtual source is moved around so that it emits scattered beams of which some pass through an object, some bypass the object and some reflect off the object. The bypass beams and the reflected beams interfere with one another in an interference zone to provide an image which can be seen as a Fresnel Fringe, by defocusing the image.

While example embodiments have been described in connection with what is presently considered to be an example of a possible most practical and/or suitable embodiment, it is to be understood that the descriptions are not to be limited to the disclosed embodiments, but on the contrary, is intended to cover various modifications and equivalent arrangements included within the spirit and scope of the example embodiment. Those skilled in the art will recognize or be able to ascertain using no more than routine experimentation, many equivalents to the specific example embodiments specifically described herein. Such equivalents are intended to be encompassed in the scope of the claims, if appended hereto or subsequently filed.

The invention claimed is:

1. A method of imaging an object within a first material within a patient's body, the first material having a different density to the object, the method comprising: emitting no more than a single acoustic coherent beam; focusing the acoustic coherent beam to a virtual acoustic source in a fluid or an amorphous second material outside of the first material; moving the virtual acoustic source in the fluid or amorphous material such that at least a plurality of scattered beams from the virtual acoustic source scan the first material and at least one scattered beam is reflected from the object to form a reflected beam and at least one scattered beam bypasses the object to form a bypass beam, and wherein the reflected beam and the bypass beam intercept one another to form a coherent interference zone; moving an acoustic detector towards and away from the object using a detector actuator to defocus the coherent interference zone to provide a Fresnel fringe; and a processor forming the image of the object from the Fresnel fringe.

2. The method of claim 1, wherein the focusing the acoustic coherent beam is effected by a focusing mirror.

3. The method of claim 2, further comprising the processor applying a defocus amount, delta f, to sharpen at least one feature of the image.

4. The method of claim 1, wherein the object is identified as a tumour in the patient's body.

5. The method of claim 4, wherein the acoustic coherent beam is focused to the virtual acoustic source in the fluid or amorphous second material which is in the patient's body.

6. The method of claim 4, wherein the acoustic coherent beam is focused to the virtual acoustic source in a fluid outside of the patient's body in which at least a part of the patient's body is immersed.

* * * * *